(12) United States Patent
Zamora (10) Patent No.: US 9,726,589 B2
(45) Date of Patent: Aug. 8, 2017

(54) APPARATUS AND METHOD TO MEASURE A PROPERTY OF WELLBORE FLUID

(71) Applicant: M-I L.L.C., Houston, TX (US)

(72) Inventor: Mario Zamora, Houston, TX (US)

(73) Assignee: M-I L.L.C., Houston, TX (US)

( * ) Notice: Subject to any disclaimer, the term of this patent is extended or adjusted under 35 U.S.C. 154(b) by 470 days.

(21) Appl. No.: 14/212,063

(22) Filed: Mar. 14, 2014

(65) Prior Publication Data

US 2014/0260560 A1    Sep. 18, 2014

Related U.S. Application Data

(60) Provisional application No. 61/782,102, filed on Mar. 14, 2013, provisional application No. 61/782,049, filed on Mar. 14, 2013.

(51) Int. Cl.
*G01N 11/14*    (2006.01)

(52) U.S. Cl.
CPC .................................. *G01N 11/14* (2013.01)

(58) Field of Classification Search
CPC ..................................................... G01N 11/14
USPC .................................. 73/54.28, 54.31, 54.35
See application file for complete search history.

(56) References Cited

U.S. PATENT DOCUMENTS

| | | | | |
|---|---|---|---|---|
| 2,592,378 A | * | 4/1952 | Chaney | E21B 47/101 73/152.32 |
| 3,229,506 A | * | 1/1966 | Bruss | G01N 11/04 73/54.28 |
| 4,571,988 A | * | 2/1986 | Murphy, Jr. | G01N 11/14 73/54.33 |
| 4,612,800 A | * | 9/1986 | Erian | B01F 3/1221 73/54.01 |
| 5,677,481 A | * | 10/1997 | Brown | B41J 2/195 137/92 |
| 6,629,451 B1 | * | 10/2003 | Taylor | G01N 11/14 73/54.28 |
| 2003/0154772 A1 | * | 8/2003 | Jackson | G01N 11/14 73/54.28 |
| 2004/0149019 A1 | * | 8/2004 | Johnson | G01N 11/14 73/54.28 |
| 2005/0066710 A1 | * | 3/2005 | Lin | G01N 11/02 73/54.42 |
| 2005/0141338 A1 | * | 6/2005 | Jarvinen | B28C 7/026 366/2 |
| 2010/0004890 A1 | * | 1/2010 | Tonmukayakul | G01N 11/14 702/113 |
| 2010/0018294 A1 | * | 1/2010 | Tonmukayakul | G01N 33/241 73/54.28 |

(Continued)

*Primary Examiner* — Daniel S Larkin
*Assistant Examiner* — Anthony W Megna Fuentes
(74) *Attorney, Agent, or Firm* — Sara K. M. Hinkley (57) ABSTRACT

A method includes disposing an open end of a housing in a wellbore fluid, flowing the wellbore fluid into the housing though the open end, rotating an impeller disposed within the housing at a first rotational speed with a motor coupled to the impeller, and determining at least one of viscosity and rheology of the wellbore fluid based on the rotating an impeller. An apparatus includes a housing, a mechanical agitator disposed in the housing, a motor operatively coupled to the mechanical agitator, a first sensor coupled to at least one of the mechanical agitator and the motor, and a second sensor disposed in the housing and configured to measure a fluid property or characteristic.

20 Claims, 4 Drawing Sheets

(56) References Cited

U.S. PATENT DOCUMENTS

2013/0118235 A1\* 5/2013 Morgan ................ G01N 11/14
73/54.28

\* cited by examiner

APPARATUS AND METHOD TO MEASURE A PROPERTY OF WELLBORE FLUID

CROSS-REFERENCE TO RELATED APPLICATIONS

This application, pursuant to 35 U.S.C. §119(e), claims priority to U.S. Provisional Application Ser. No. 61/782,049, filed Mar. 14, 2013 and U.S. Provisional Application Ser. No. 61/782,102, filed Mar. 14, 2013. Both applications are incorporated by reference in their entirety.

BACKGROUND

In drilling operations for the exploration of oil and gas, various fluids are used during different stages of drilling, production, and completion of a well. For example, a liquid slurry known as drilling fluid (i.e., drilling mud) is used for maintenance and lubrication of the borehole created during the drilling operation. The fluids used may be referred to as wellbore fluids, which may include drilling fluids, production fluids, and completion fluids. A wellbore fluid system of a well includes a mud holding tank at the well surface located on or adjacent to the drilling rig and a network of pumps, mixers, and fluid supply lines. During drilling operations, wellbore fluid is pumped from the mud holding tank, through the fluid supply lines, down through the wellbore and circulated at a desired rate, and is returned to the surface of the wellbore. The returned wellbore fluid carries with it drill cuttings from the bottom of the borehole produced as drilling advances. As such, during this circulation, the wellbore fluid may act to remove drill cuttings from the bottom of the hole to the surface, but may also be used to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

When the circulating wellbore fluid, along with the carried drill cuttings is returned to the surface, it is delivered to a screening device known as a shaker that serves as a sieve for removing the carried drilling cuttings from the wellbore fluid. When the drill cuttings have been removed from the wellbore fluid by the shaker, the wellbore fluid is returned to the mud storage tank for reuse. The drill cuttings separated from the wellbore fluid are collected and conveyed to storage tanks for treatment and disposal.

In most rotary drilling procedures, the wellbore fluid takes the form of a "mud," i.e., a liquid having solids suspended therein. The solids function to impart desired rheological properties to the wellbore fluid and also to increase the density thereof in order to provide a suitable hydrostatic pressure at the bottom of the well. The drilling mud may be either a water-based or an oil-based mud. As such, the ability to suspend drilling cutting to reduce wear on the drill bit depends on the rheological properties of the drilling mud related to the viscosity of the wellbore fluid.

Wellbore fluids, including drilling muds, may consist of polymers, biopolymers, clays and organic colloids added to a water-based fluid to obtain the desired viscous and filtration properties. Heavy minerals, such as barite or calcium carbonate, may be added to increase density. Solids from the formation are incorporated into the mud and often become dispersed in the mud as a consequence of drilling. Further, wellbore fluids may contain one or more natural and/or synthetic polymeric additives, including polymeric additives that increase the rheological properties (e.g., plastic viscosity, yield point value, gel strength) of the drilling mud, and polymeric thinners and flocculents.

However, during the drilling process, the wellbore fluid may need to be monitored and/or altered frequently. For example, depending on the current drilling conditions, changes to the viscosity of the wellbore fluid may be critical, particularly when drilling deviated and/or horizontal wellbores. Previous techniques to determine the viscosity of wellbore fluids employ running the drilling mud through a calibrated funnel, such as a Marsh funnel, to record the time it takes to have the drilling mud pass through the funnel. Other techniques involve pumping samples of drilling mud from the mud pits at the surface of the well to measurement units, requiring additional plumping and maintenance for the measurement units.

DETAILED DESCRIPTION

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

Embodiments disclosed herein generally relate to a method and apparatus to measure a property of a fluid. More specifically, embodiments disclosed herein relate to a method and apparatus having multiple sensors included therewith to calculate, determine, measure, and otherwise monitor one or more properties of a fluid.

In one aspect, embodiments disclosed herein relate to an apparatus, kit, and/or method to measure a property, e.g., viscosity or rheology, of a fluid that may be usable in a wellbore. The wellbore fluid may be disposed within a mud pit, such as adjacent or on a drilling rig, may be disposed within a mixing tank, or the like. Embodiments disclosed herein may then be incorporated with the mud pit or the mixing tank to measure, determine, and/or otherwise monitor one or more properties of the wellbore fluid.

Generally, embodiments disclosed herein relate to an apparatus and method of using the apparatus to determine one or more properties of a fluid. The apparatus includes a housing in which the fluid is disposed. The housing may be submerged (partially or fully) into a tank having fluid or the fluid may be disposed in or flowed through the housing. The housing may include one or more sensors configured to measure one or more properties or characteristics of the fluid. For example, the sensors may measure density, temperature, viscosity, rheology, acidity, resistivity, bridging/fluid loss, electrical stability, emulsion stability, and/or capacitance of the fluid. A mechanical mixer or agitator, such as an impeller, may be disposed in the housing and configured to agitate the fluid disposed therein so that the viscosity or rheology of the fluid may be measured.

A method in accordance with one or more embodiments of the present disclosure may include disposing an open end of a housing in a wellbore fluid, flowing the wellbore fluid into the housing though the open end, rotating an impeller disposed within the housing at a first rotational speed with a motor coupled to the impeller, and determining at least one of viscosity and rheology of the wellbore fluid based on the rotating an impeller.

An apparatus in accordance with one or more embodiments of the present disclosure may include a housing, a mechanical agitator disposed in the housing, a motor operatively coupled to the mechanical agitator, a first sensor coupled to at least one of the mechanical agitator and the motor, and a second sensor disposed in the housing and configured to measure a fluid property or characteristic.

The apparatus may include a housing configured to accommodate the one or more sensors such that a single apparatus may be used to measure various properties or characteristics of a fluid. The housing may be configured to be immersed in a tank, pit, or the like so that a fluid can be monitored and the quality of the fluid maintained in response to data received from the one or more sensors. A control module or computer may be coupled to the sensors and include algorithms to automatically process signals from the one or more sensors to analyze and validate the measured data in real-time.

A system in accordance with one or more embodiments of the present disclosure may include a tank, a housing disposed in the tank, the housing having an open end, an impeller rotatably disposed within the housing, a motor coupled to the impeller and configured to rotate the impeller at a rotational speed within the housing, and a sensor coupled to the motor and configured to measure a power usage of the motor when rotating the impeller.

In one or more embodiments, the apparatus may include a sensor coupled to a mechanical mixer or agitator to measure the viscosity or rheology of the fluid. For example, the housing of the apparatus may include an impeller disposed therein and coupled to a motor. The housing may have an open end and an axis defined therethrough. The open end of the housing may be disposed within the fluid that is being measured. The impeller is configured to rotate within the housing to agitate the fluid inside the housing. A central axis of the impeller may be substantially aligned with the axis of the housing to provide uniform movement or agitation of the fluid within the housing. The motor is coupled to the impeller and may be configured to rotate the impeller at different rotational speeds within the housing. A sensor may be coupled to the motor and configured to measure power usage of the motor when rotating the impeller. The measured power usage may be sent to a control module or computer to calculate the viscosity of the fluid or determine the rheology of the fluid.

The housing may include a plurality of apertures formed therethrough, e.g., formed through a wall(s) of the housing. Thus, when the housing is immersed in a tank of fluid, the fluid may enter the housing through the plurality of apertures. Further, the mechanical mixer or agitator may be any type of mechanical mixer or agitator known in the art, for example, a helical impeller, a paddle impeller, or a propeller impeller. In one embodiment, the impeller may be a pitched paddle impeller, in which the impeller may include a plurality of paddle blades with at least one of the paddle blades pitched at an angle of about 15 degrees with respect to the axis of the impeller and/or having an aperture formed therethrough. In other embodiments, the impeller may be a helical screw impeller having a helical screw blade. Further, the apparatus may include at least one more sensor, such as a second sensor, disposed within the cylindrical housing and configured to measure at least one of density, temperature, acidity, resistivity, bridging/fluid loss, electrical stability, emulsion stability, and capacitance of the fluid.

In one or more embodiments, one or more sensors may be disposed inside the housing and one or more sensors may be coupled to the housing. For example, the apparatus may include a housing in which a first sensor and a second sensor are disposed and a third sensor is coupled to the housing. The first sensor may be used to measure density of the fluid, the second sensor may be used to measure temperature of the fluid, and the third sensor may be used to measure viscosity and rheology of the fluid. As such, the first sensor may include a differential-pressure cell, the second sensor may include a thermocouple, and the third sensor may include and/or be coupled to an impeller.

The apparatus may further include a fourth sensor, a fifth sensor, a sixth sensor, and a seventh sensor, or even more sensors, disposed within and/or included with the housing. The fourth sensor may be used to measure acidity of the fluid, the fifth sensor may be used to measure resistivity of the fluid, the sixth sensor may be used to measure capacitance of the fluid, and the seventh sensor may be used to measure electrical stability of the fluid. As such, the fourth sensor may include a pH meter, the fifth sensor may include a resistivity meter, the sixth sensor may include a capacitance meter, and the seventh sensor may include an electrical stability meter. One of ordinary skill in the art will understand that any number of sensors may be disposed in or coupled to a housing of an apparatus in accordance with the present disclosure and any type of sensor known in the art for measuring a particular property or characteristic of a fluid may be used.

Figure 1:
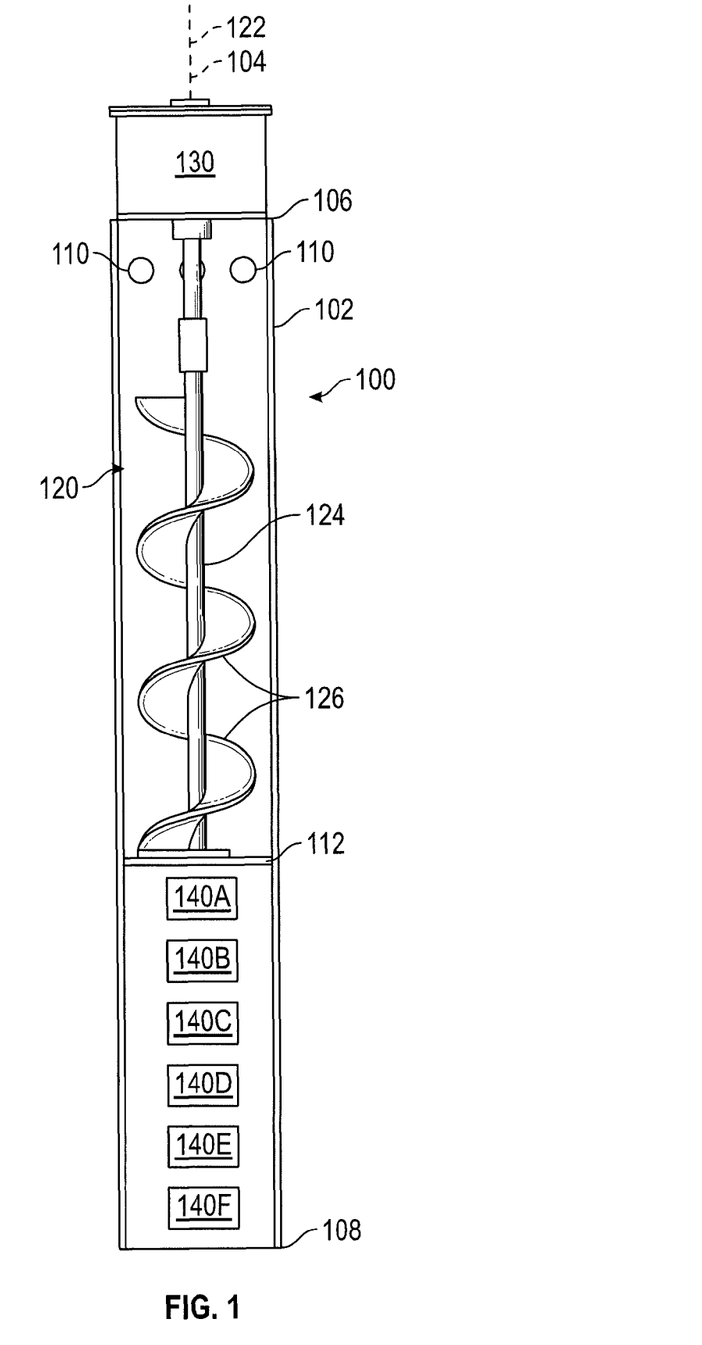
FIG. 1 shows a cross-sectional view of an apparatus in accordance with embodiments disclosed herein.

Referring now to FIG. 1, a cross-sectional view of an apparatus 100 to measure a property of a fluid for a well in accordance with embodiments disclosed herein is shown. The apparatus 100 includes a housing 102 having an axis 104 defined therethrough. As shown, the housing 102 may be a cylindrical housing, though any shaped housing may be used. At least one end of the housing 102 is open. As used herein, an open end of the housing 102 refers to an end of the housing that allows fluid flow into or out of the housing. An open end may be completely open, i.e., the size of the opening (e.g., diameter) in the end of the housing is approximately equal to the size (e.g., diameter) of the housing. As shown in FIG. 1, the housing 102 may include a first end 106 (e.g., top end) and a second end 108 (e.g., bottom end) with both the first end 106 and the second end 108 open. In other embodiments, one or both ends of the housing may be partially open. For example, one or both ends of the housing may include one or more openings formed therein such that fluid flow through the ends of the housing may be allowed, but through a restriction or opening smaller than the diameter of the housing. The housing 102 may also include a plurality of apertures 110 formed therethrough (i.e., through a wall(s) of the housing) to permit the fluid to flow into the housing 102 when the housing 102 is immersed in the fluid.

The apparatus 100 may be used to measure a property of a fluid, such as a wellbore fluid. The apparatus 100 may include multiple sensors that measure various properties and characteristics of fluid. In one embodiment, the apparatus 100 may be configured to measure the viscosity or rheology of the fluid. In such an embodiment, the apparatus 100 may include an impeller 120 disposed within the housing 102 and having an axis 122 defined therethrough. The impeller 120 is rotatably disposed within the housing 102, such that the impeller 120 may rotate about the axis 122 within and with respect to the housing 102. The impeller 120 includes a shaft 124 with at least one blade 126 attached thereto. One of ordinary skill in the art will appreciate that the impeller 120 may be any impeller known in the art for rotating or agitating a fluid, such as, for example, a helical impeller, a paddle impeller, or a propeller impeller. In one embodiment, the axis 122 of the impeller 120 may substantially align with the axis 104 of the housing 102, and the shaft 124 of the impeller 120 may substantially align with the axis 104 of the cylindrical housing 102.

The impeller 120 may be connected to the housing 102 to support the impeller 120. As shown in FIG. 1, the impeller 120 is pivotally connected to a support member 112 extending across the housing 102. The support member 112 is used to pivotally support the impeller 120, but also enables fluid flow therethrough such that wellbore fluid may flow into the housing 102 through the plurality of apertures 110 and out of the cylindrical housing 102 through the second end 108.

A motor 130 may be included within the apparatus 100 and coupled to the impeller 120 to rotate the impeller 120. Particularly, as shown, the motor 130 may be connected to the first end 106 of the housing 102, with the motor 130 coupled to the shaft 124 of the impeller 120 to rotate the impeller 120. The motor 130 may be coupled to the first end 106 of the housing 102, such that the first end 106 is closed. The motor 130 may be used to rotate the impeller 120 at different rotational speeds within the housing 102, such as by having the motor 130 rotate the impeller 120 at a first rotational speed and a second rotational speed. For example, the motor 130 may be used to rotate the impeller 120 at rotational speeds ranging from about 30 rpm up to about 600 rpm, depending upon the fluid being evaluated with the apparatus 100. As such, the motor 130 may be a variable frequency drive motor, a stepper motor, or any other type of motor known in the art that may be used to rotate the impeller 120 at different rotational speeds.

The apparatus 100 may also include one or more sensors to measure various properties and characteristics of one or more components of the apparatus 100. For example, a sensor may be coupled to the motor 130 to measure power usage of the motor 130 when rotating the impeller 120. This sensor may be included with the motor 130, such as disposed within the housing of the motor 130, in which the sensor may measure the power usage of the motor 130 when the motor 130 is rotating the impeller 120 at different rotational speeds. As such, in one embodiment, the sensor may be used to measure the power usage of the motor 130 when rotating the impeller 120 at a first rotational speed, and then may be used to measure the power usage of the motor 130 when rotating the impeller 120 at a second rotational speed. In one or more embodiments of the present disclosure, the power usage of the motor at different rotational speeds may be used to calculate, determine, or otherwise measure viscosity and/or rheology of the fluid for use within a well. In some embodiments, the torque and rotational speed of the impeller 120 may be observed or sensed by a sensor and used to determine viscosity and/or rheology of the fluid.

In addition to having a sensor that measures various properties and characteristics of the apparatus 100, such as measure the power usage of the motor 130, the apparatus 100 may include one or more additional sensors coupled thereto to measure various properties and characteristics of fluid. As shown in FIG. 1, one or more sensors 140A-F may be included with the apparatus 100, in which the sensors 140A-F may be disposed within or proximate the housing 102 of the apparatus 100 to measure various properties and characteristics of the fluid being evaluated with the apparatus 100. The sensors 140A-F may be used to measure, for example, density, temperature, acidity, resistivity, bridging/fluid loss, electrical stability, emulsion stability, and/or capacitance of the fluid.

In one embodiment, four sensors may be disposed in the housing 102. For example, the sensor 140A may be used to measure density of the wellbore fluid, the sensor 140B may be used to measure temperature of the wellbore fluid, the sensor 140C may be used to measure acidity of the wellbore fluid, and/or the sensor 140D may be used to measure capacitance of the wellbore fluid. As such, the sensor 140A may be a differential-pressure cell to measure density, the sensor 140B may be a thermocouple to measure temperature, the sensor 140C may be a pH meter to measure acidity, and the sensor 140D may be a capacitance meter to measure capacitance. Those having ordinary skill in the art, however, will appreciate that other sensors may be used in addition, or in the alternative, to the sensors discussed above to measure various properties and characteristics of wellbore fluid.

In another example, six sensors 140A-F may be included with the apparatus 100, such as by having the sensors 140A-F disposed within and/or coupled to the housing 102. This arrangement may enable the sensors 140A-F to measure various properties and characteristics of the fluid being evaluated with the apparatus 100. In this example, the sensor 140A may be used to measure density of the fluid, the sensor 140B may be used to measure temperature of the fluid, the sensor 140C may be used to measure acidity of the fluid, the sensor 140D may be used to measure resistivity of the fluid, the sensor 140E may be used to measure capacitance of the fluid, and/or the sensor 140F may be used to measure electrical stability of the fluid. As such, the sensor 140A may include a differential-pressure cell to measure density, the sensor 140B may include a thermocouple to measure temperature, the sensor 140C may include a pH meter to measure acidity, the sensor 140D may include a resistivity meter to measure resistivity, the sensor 140E may include a capacitance meter to measure capacitance, and/or the sensor 140F may include an electrical stability meter to measure electrical stability. Those having ordinary skill in the art, however, will appreciate that other sensors may be used in addition, or in the alternative, to the sensors discussed above to measure various properties and characteristics of wellbore fluid.

As discussed above, the apparatus 100 may be used to measure a property of a wellbore fluid, including the viscosity and rheology of the wellbore fluid. As such, the apparatus may be incorporated with or placed into a mud pit, a mixing tank, or the like, to measure, determine, and/or otherwise monitor the one or more properties of the wellbore fluid included within the mud pit, mixing tank, or the like. For example, when using the apparatus 100, the second end 108 of the apparatus 100, at least, may be disposed within the wellbore fluid such that the wellbore fluid is exposed to the sensors 140A-F and is at least partially exposed to the impeller 120 of the apparatus 100. However, as the housing 102 includes the plurality of apertures 110 formed adjacent to the first end 106 of the housing 102, the apparatus 100 may be disposed within the wellbore fluid to have the wellbore fluid flow in through the plurality of apertures 110 and into the housing 102.

With the apparatus 100 exposed to the wellbore fluid, one or more of the sensors included with the apparatus 100 may be used to measure one or more properties of a wellbore fluid for a well. For example, one or more of the sensors 140A-F may be used to measure density, temperature, acidity, resistivity, bridging/fluid loss, electrical stability, emulsion stability, and/or capacitance of the wellbore fluid. In some embodiments, the impeller 120 of the apparatus 100 may be rotated with the motor 130, with the sensor coupled thereto measuring the power usage of the motor 130. The impeller 120 may be rotated at one or more rotational speeds within the housing 100, enabling the sensor coupled to the motor 130 to determine and measure viscosity and/or rheology of the wellbore fluid exposed to the apparatus 100. Further, as the sensors 140A-F are shown as disposed closer to the second end 108 of the housing 102, the impeller 120 may be rotated to promote circulation of the wellbore fluid down and across the sensors 140A-F, and out through the second end 108 of the housing 102.

As shown in FIG. 1, the housing 102 includes the plurality of apertures 110 disposed adjacent to the first end 106 thereof to enable fluid flow through the housing 102. However, those having ordinary skill in the art will appreciate that any number and arrangement of apertures may be included within the housing of the apparatus without departing from the scope of the present disclosure. For example, with reference to FIG. 2, a housing 202 with a shaft 224 of an impeller 220 extending therefrom is shown having a plurality of apertures 210 in accordance with embodiments of the present disclosure. The housing 202 includes the plurality of apertures 210 formed along the length of the housing 202, thereby increasing fluid flow within the housing 202. Accordingly, those having ordinary skill in the art will appreciate that any housing having any number and/or arrangement of apertures may be used within one or more embodiments of the present disclosure. As such, the housing and the apertures may be sized and configured to enable and/or inhibit different types of fluid flow through and within the housing of the apparatus, such as by inducing turbulent and/or laminar flow for the wellbore fluid within the apparatus, depending on the desired characteristics for the wellbore fluid used with the apparatus of the present disclosure. An example of a housing of the apparatus in accordance with the present disclosure may be provided by or available from Epoch Well Services, Inc. (Houston, Tex.).

Further, with reference back to FIG. 1, the impeller 120 including the shaft 124 with at least one blade 126 connected thereto is shown as a helical screw blade impeller having a helical screw blade. Those having ordinary skill in the art, however, will appreciate that other types and forms of impellers may be used without departing from the scope of the present disclosure. For example, with reference to FIG. 3, an impeller 320 with an axis 322 defined therethrough is shown having a shaft 324 with a plurality of blades 326 connected thereto in accordance with embodiments of the present disclosure.

Figures 2, 3:
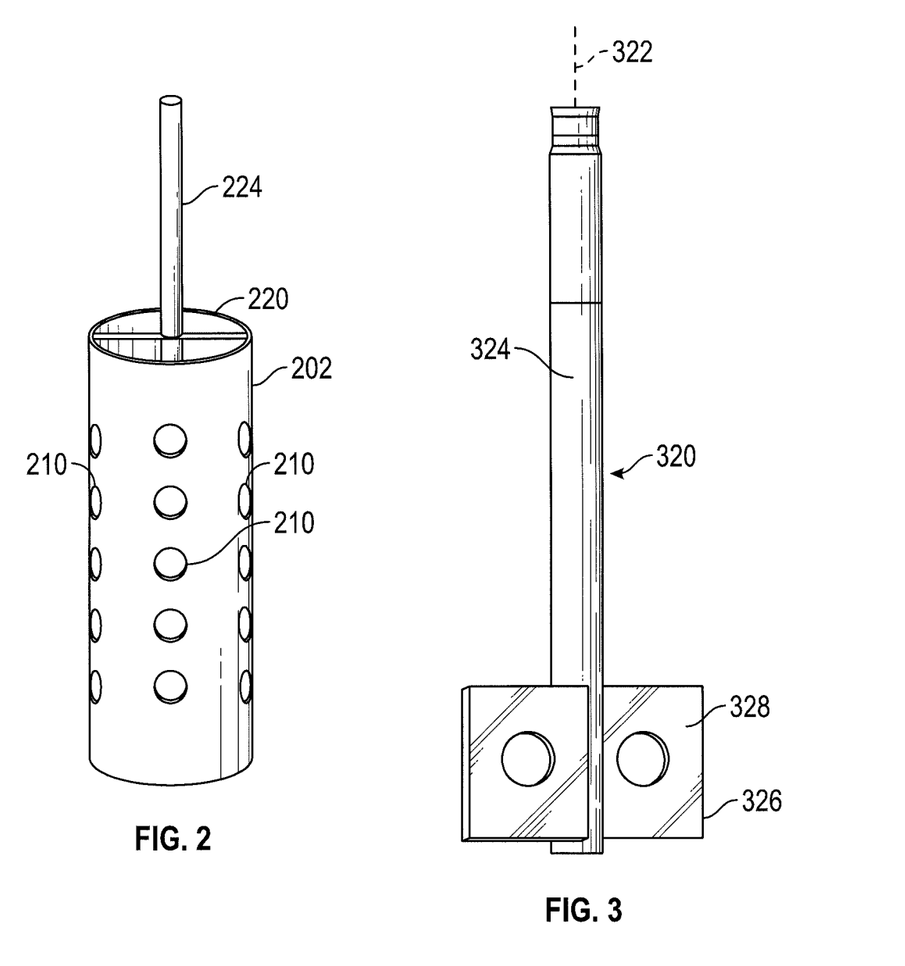
FIG. 2 shows a perspective view of a cylindrical housing for an apparatus in accordance with embodiments disclosed herein.
FIG. 3 shows a perspective view of an impeller for an apparatus in accordance with embodiments disclosed herein.

In FIG. 3, the impeller 320 is shown as a pitched paddle impeller having two paddle blades 326 connected to the shaft of the impeller. The paddle blades 326 are pitched with respect to the impeller 320, in that the paddle blades 326 are angled with respect to the axis 322 and the shaft 324 of the impeller 320. As such, in one embodiment, one or more of the paddle blades may be pitched between an angle of about 5 degrees and about 30 degrees with respect to the shaft or axis of the impeller, such as pitched at an angle of about 15 degrees with respect to the shaft or axis of the impeller. Further, one or more of the paddle blades may have an aperture formed therethrough. However, those having ordinary skill in the art will appreciate that other types and forms of impellers may be used without departing from the scope of the present disclosure. An example of a pitched impeller of the apparatus in accordance with the present disclosure may be provided by or available from Thermo Fisher Scientific (Waltham, Mass.).

Figure 4:
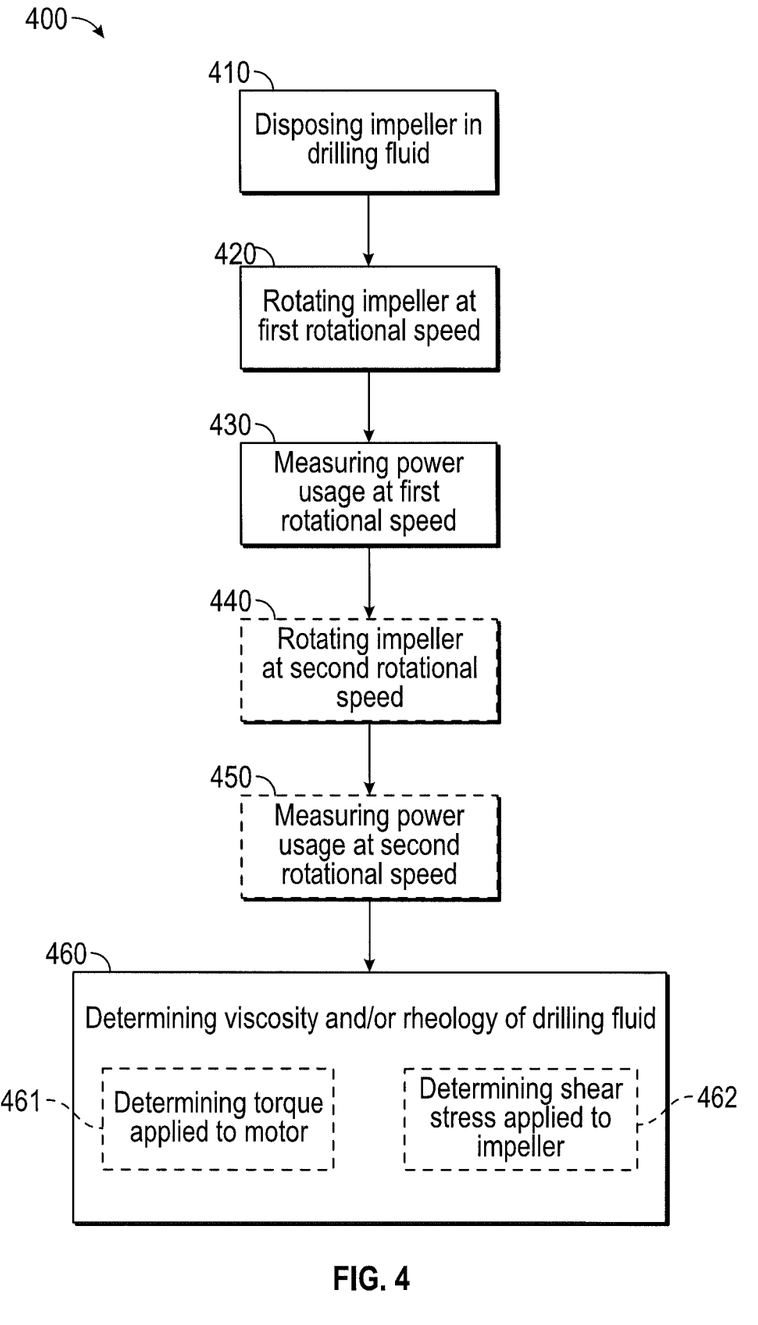
FIG. 4 shows a diagram of a flow chart of a method in accordance with embodiments disclosed herein.

As discussed above, an apparatus in accordance with the present disclosure may be used to measure viscosity and/or rheology of a wellbore fluid, in addition to measuring other properties and characteristics of the wellbore fluid. Referring now to FIG. 4, a diagram of a flow chart of a method 400 to measure viscosity and/or rheology of a wellbore fluid for a well using an apparatus as disclosed herein with respect to FIGS. 1-3 is shown. As such, the method 400 may be implemented by a component of the apparatus in accordance with the present disclosure, such as by having a sensor or a computer disposed within the apparatus execute one or more steps of the method 400 discussed below. Alternatively, or additionally, the method 400 may be implemented by a component coupled or connected to the apparatus, such as a by having a computer operatively coupled to a sensor of the apparatus execute one or more steps of the method 400 discussed below.

The method 400 begins with step 410, disposing an impeller of the apparatus within the wellbore fluid, as discussed above, and then follows with step 420, rotating the impeller at a first rotational speed. The impeller is rotated at the first rotational speed with the motor coupled to the impeller, and in step 430, a sensor coupled to the motor measures the power usage of the motor when rotating the impeller at the first rotational speed.

After measuring the power usage of the motor at the first rotational speed in step 430, the method 400 may proceed to step 440, rotating the impeller at a second rotational speed within the wellbore fluid. The impeller is rotated at the second rotational speed with the motor coupled to the impeller, and in step 450, the sensor coupled to the motor measures the power usage of the motor when rotating the impeller at the second rotational speed. The viscosity and/or rheology of the wellbore fluid may then be determined in step 460 based upon the power usage measured by the sensor is step 430 and/or step 450. For example, as the power usage of the motor is being measured and is known using the sensor, and the rotational speed of the impeller is known (such as by having the rotational speed of the impeller preset or measured), torque applied to the motor through the impeller may be determined, in step 461, as follows, with P representing power, T representing torque, and ω representing rotational speed:

$$P = T \times \omega \qquad \text{Equation 1}$$

After determining torque applied to the motor through the impeller, shear stress applied to the impeller through the wellbore fluid may be determined in step 462 based upon the torque. For example, as the torque applied to the motor has been determined and is known, the area of the impeller exposed to the wellbore fluid is known (such as by having the exposed area of the impeller preset or measured), and the radius of the impeller is known (such as by having the radius of the impeller preset or measured), the shear stress applied to the impeller may be determined, as follows, with F representing the force applied through the impeller, T representing shear stress, A representing the area of the impeller exposed to the wellbore fluid, and r representing the radius of the impeller:

$$T = F \times r \qquad \text{Equation 2}$$

$$\tau = \frac{F}{A} \qquad \text{Equation 3}$$

$$\tau = \frac{T}{A \times r} \qquad \text{Equation 4}$$

As such, the power used by the motor to rotate and drive the impeller within the wellbore fluid may be converted from torque to shear stress to approximate viscosity of the wellbore fluid. Particularly, as shear stress is directly proportional to viscosity, the viscosity of the wellbore fluid may be determined based upon measuring the power required to rotate and drive an impeller within the wellbore fluid at a particular speed. Further, as the viscosity of the wellbore fluid is being approximated for rotating the impeller at different rotational speeds, the change in the viscosity at the different rotational speeds may be used to determine the rheology of the wellbore fluid. Particularly, as rheology relates to a study of the flow of matter, rheology is used to account for the behavior of non-Newtonian fluids, in which the viscosity of a fluid may change with strain rate (or relative velocity of the fluid). As such, the change in the viscosity at the different rotational speeds may be used to determine the rheology of the wellbore fluid.

An apparatus in accordance with one or more embodiments of the present disclosure may be used and operated in continuous mode or in batch mode. For example, the apparatus may be disposed within a mud pit to continuously measure the power usage of the motor to rotate the impeller, thereby enabling the apparatus to continuously determine and measure viscosity and/or rheology of the wellbore fluid within the mud pit. Additionally, or alternatively, the sensors 140A-F included within the apparatus may be used to continuously determine and measure density, temperature, acidity, resistivity, bridging/fluid loss, electrical stability, emulsion stability, and/or capacitance of the wellbore fluid within the mud pit. This may enable the apparatus to measure, determine, and monitor one or more properties of the wellbore fluid in real-time.

Further, the apparatus may be calibrated with different wellbore fluids to enable the apparatus for use with various wellbore fluids. For example, with respect to FIG. 1, the impeller 120 of the apparatus 100 may be rotated by the motor 130 within fluid to rotate at a first rotational speed, at a second, higher rotational speed, and/or a third, lower rotational speed to have the apparatus 100 measure and determine viscosity and/or rheology of the fluid with respect to these different rotational speeds. The measured and determined viscosity and/or rheology may then be compared with known values to calibrate the apparatus. As such, rheology determined for the wellbore fluid may be used to generate and provide other properties of the wellbore fluid, such as plastic viscosity and/or yield point.

It should be understood that the present disclosure contemplates having other structures and/or arrangements for an apparatus to measure a property of a wellbore fluid for a well. For example, in other embodiments, the apparatus may have the impeller and the sensors arranged differently within the housing, such as by having the sensors disposed closer to the top end of the housing with the impeller disposed closer to the bottom end of the housing. As such, those having ordinary skill in the art will appreciate other configurations may be used for an apparatus to measure viscosity and rheology without departing from the scope of the present disclosure.

Figure 5:
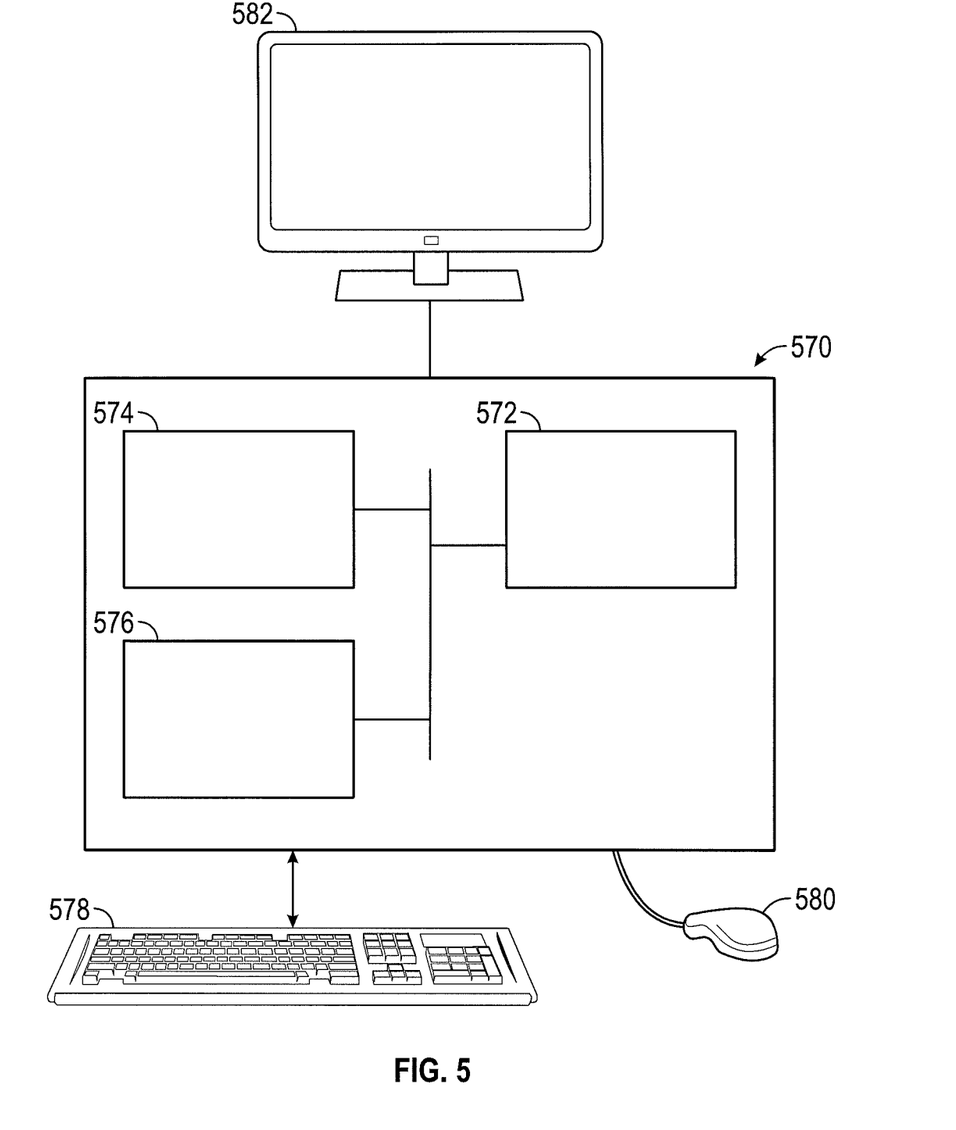
FIG. 5 shows a computer system in accordance with embodiments disclosed herein.

Aspects of embodiments disclosed herein, such as when using a sensor to measure viscosity and/or rheology of a wellbore fluid, may be implemented on any type of computer, regardless of the location of the computer, the size of the computer, the platform used with the computer, and/or other characteristics commonly varied amongst computers. For example, as shown in FIG. 5, a networked computer system 570 that may be used in accordance with an embodiment disclosed herein includes a processor 572, associated memory 574, a storage device 576, and/or numerous other elements and functionalities typical of today's computers (not shown). The networked computer system 570 may also include input means, such as a keyboard 578 and/or a mouse 580, and/or may include output means, such as a monitor 582. The networked computer system 570 may be connected to a local area network (LAN) or a wide area network (e.g., the Internet) via a network interface connection (not shown). Those skilled in the art will appreciate that these input and output means may take many other forms. Additionally, the computer system may not be connected to a network. Further, those skilled in the art will appreciate that one or more elements of the computer system 570 may be located at a remote location and/or connected to the other elements over a network.

Accordingly, aspects of the present disclosure contemplate using a computer with an apparatus to measure a property of a wellbore fluid. For example, a computer may be used to compute algorithms, in which the computer may then be used to determine the property of the wellbore fluid in real-time. The computer may then be used to auto process signals, such as validate and analyze measured data provided from the sensors in real-time. Thus, the measured data may be compared against desired data. For example, the measured or determined viscosity of the wellbore fluid may be compared against the desired viscosity of the wellbore fluid before use in a particular application, e.g., as a drilling fluid. A makeup of the wellbore fluid can then be adjusted, for example, chemical additives may be added to the wellbore fluid or the fluid may be diluted, until the measured fluid property or characteristic corresponds to the desired fluid property or characteristic. The computer may be electronically coupled to one or more of the sensors of the apparatus of the present disclosure, in which the computer, or at least one or more components of the computer, may be included within the apparatus itself. For example, a processor for a computer, or related circuitry, may be included within the motor housing of the apparatus to be electronically coupled to one or more sensors of the apparatus. As such, the present disclosure contemplates multiple arrangements and configurations for an apparatus to measure a property of a wellbore fluid in accordance with the present disclosure.

Embodiments disclosed herein may provide an apparatus that may be portable, such as by having the apparatus disposed directly within a mud pit and/or mixing tank. This may reduce the need for equipment to pump and sample wellbore fluid from the mud pit or mixing tank to the measuring equipment. Further, embodiments disclosed herein may provide an apparatus that is cost efficient and robust, thereby reducing the need to replace and maintain expensive measuring equipment. Furthermore, embodiments disclosed herein may provide an apparatus that may be used to measure, determine, and/or otherwise monitor one or more properties of a wellbore fluid in real-time, in addition to other wellbore fluid properties. As such, the apparatus may be coupled to a control panel, or other appropriate equipment, to enable a user to review the results and measurements provided by the apparatus of the present disclosure.

One or more embodiments disclosed herein relate to an apparatus to measure a property of a fluid for a wellbore. The apparatus may include a housing to be disposed within the wellbore fluid, a first sensor disposed within the housing to measure density of the wellbore fluid, a second sensor disposed within the housing to measure temperature of the wellbore fluid, and a third sensor coupled to the housing to measure viscosity and rheology of the wellbore fluid.

In another aspect, embodiments disclosed herein relate to a kit to measure a property of a wellbore fluid for a well. The kit includes a housing to be disposed within the wellbore fluid, a first sensor disposed within the housing to measure density of the wellbore fluid, a second sensor disposed within the housing to measure temperature of the wellbore fluid, and a third sensor coupled to the housing to measure viscosity and rheology of the wellbore fluid. The kit further includes at least one of a fourth sensor disposed within the housing to measure acidity of the wellbore fluid, a fifth sensor disposed within the housing to measure resistivity of the wellbore fluid, a sixth sensor disposed within the housing to measure capacitance of the wellbore fluid, and a seventh sensor disposed within the housing to measure electrical stability of the wellbore fluid.

In another aspect, embodiments disclosed herein relate to a method to manufacture an apparatus to measure a property of a wellbore fluid for a well. The method may include disposing a first sensor within a housing to measure density of the wellbore fluid, the housing to be disposed within the wellbore fluid, disposing a second sensor within the housing to measure temperature of the wellbore fluid, and coupling a third sensor to the housing to measure viscosity and rheology of the wellbore fluid.

In another aspect, embodiments disclosed herein relate to a method to measure a property of a wellbore fluid for a well. The method may include disposing an open end of a cylindrical housing within the wellbore fluid, the cylindrical housing having a first sensor and a second sensor disposed therein and an axis defined therethrough, the first sensor configured to measure density of the wellbore fluid and the second sensor configured to measure temperature of the wellbore fluid, rotating an impeller disposed within the cylindrical housing at a first rotational speed with a motor coupled to the impeller, an axis of the impeller substantially aligning with the axis of the cylindrical housing, and measuring at least one of viscosity and rheology of the wellbore fluid with a third sensor coupled to the motor based upon measured power usage of the motor when rotating the impeller at the first rotational speed.

Although only a few embodiments have been described in detail above, those skilled in the art will readily appreciate that many modifications are possible in the embodiments without materially departing embodiments disclosed. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words "means for" together with an associated function.

What is claimed is:

1. A method comprising: submerging an open end of a housing in a wellbore fluid; flowing the wellbore fluid into the housing through the open end; rotating an impeller disposed within the housing at a first rotational speed with a motor coupled to the impeller; and determining at least one of viscosity and rheology of the wellbore fluid based on power usage of the motor.

2. The method of claim 1, wherein the determining at least one of viscosity and rheology of the wellbore fluid based on the rotating the impeller comprises:
   measuring power usage of the motor to rotate the impeller at the first rotational speed; and
   determining at least one of viscosity and rheology of the wellbore fluid based on the power usage measured at the first rotational speed.

3. The method of claim 2, further comprising:
   determining a torque applied to the motor through the impeller based on the power usage measured at the first rotational speed;
   determining a shear stress applied on the impeller by the wellbore fluid based on the applied torque determined at the first rotational speed; and
   determining the at least one of the viscosity and the rheology of the wellbore fluid based on the applied shear stress determined at the first rotational speed.

4. The method of claim 2, further comprising:
   rotating the impeller at a second rotational speed with the motor; the second rotational speed different than the first rotational speed;
   measuring power usage of the motor to rotate the impeller at the second rotational speed; and
   determining at least one of viscosity and rheology of the wellbore fluid based on the power usage measured at the first rotational speed and the second rotational speed.

5. The method of claim 1, wherein the housing further comprises a plurality of apertures formed in a wall of the housing.

6. The method of claim 1, further comprising measuring at least one other property or characteristic of the wellbore fluid with a sensor disposed in the housing.

7. The method of claim 6, wherein rotating the impeller at the first rotational speed circulates the wellbore fluid through the housing and across the sensor.

8. The method of claim 6, wherein the at least one property or characteristic of the wellbore fluid comprises at least one of density, temperature, acidity, resistivity, bridging/fluid loss, electrical stability, emulsion stability, and capacitance.

9. The method of claim 1, further comprising comparing the determined viscosity or rheology of the wellbore fluid to a desired viscosity or rheology of the wellbore fluid.

10. The method of claim 9, further comprising adjusting a makeup of the wellbore fluid based on the comparing.

11. The method of claim 6, further comprising comparing the measured at least one other property or characteristic of the wellbore fluid with a desired property or characteristic of the wellbore fluid.

12. A method comprising: submerging a housing having an open end and a second end in a wellbore fluid, wherein at least the open end is submerged in the wellbore fluid; flowing the wellbore fluid into the housing through the open end; rotating an impeller disposed within the housing at a first rotational speed with a motor coupled to the impeller; and determining at least one of viscosity and rheology of the wellbore fluid based on a torque of the motor at the first rotational seed.

13. The method of claim 12, wherein the housing further comprises a plurality of apertures formed in a wall of the housing.

14. The method of claim 13, further comprising the wellbore fluid is introduced into the housing through at least one of the open end, the second end, and the plurality of apertures formed in the wall of the housing.

15. A method comprising: partially or fully submerging a housing, having an open end and a second end, in a wellbore fluid; introducing the wellbore fluid into the housing; rotating an impeller disposed within the housing at a first rotational speed with a motor coupled to the impeller; and determining at least one of viscosity and rheology of the wellbore fluid based on applied shear stress on the impeller at the first rotational speed.

16. The method of claim 15, wherein the wellbore fluid is introduced into the housing through at least one of the open end, the second end, and apertures formed in a wall of the housing.

17. The method of claim 16, wherein the wellbore fluid is introduced into the housing through the open end.

18. The method of claim 16, wherein the second end is open.

19. The method of claim 15, further comprising exposing the wellbore fluid to a sensor located within the housing.

20. The method of claim 19, further comprising measuring at least one other property or characteristic of the wellbore fluid with the sensor.

* * * * *